(12) United States Patent
Kuzmin et al.

(10) Patent No.: US 9,040,744 B2
(45) Date of Patent: May 26, 2015

(54) POLYCYCLIC ORGANIC COMPOUND, OPTICALLY ANISOTROPIC FILM AND METHOD OF PRODUCTION THEREOF

(75) Inventors: Valery S. Kuzmin, Moscow (RU); Alexey Nokel, Moscow (RU)

(73) Assignee: Crysoptix K.K., Tokyo (JP)

( * ) Notice: Subject to any disclaimer, the term of this patent is extended or adjusted under 35 U.S.C. 154(b) by 1578 days.

(21) Appl. No.: 12/522,914

(22) PCT Filed: Jan. 11, 2008

(86) PCT No.: PCT/EP2008/050309
§ 371 (c)(1),
(2), (4) Date: Jul. 10, 2009

(87) PCT Pub. No.: WO2008/084109
PCT Pub. Date: Jul. 17, 2008

(65) Prior Publication Data
US 2010/0215954 A1    Aug. 26, 2010

(30) Foreign Application Priority Data

Jan. 11, 2007 (GB) .................................. 0700606.7

(51) Int. Cl.

| C07D 213/34 | (2006.01) |
|---|---|
| C07D 239/26 | (2006.01) |
| C07D 498/14 | (2006.01) |
| C07D 241/12 | (2006.01) |
| C07D 271/107 | (2006.01) |
| C07D 333/76 | (2006.01) |
| C07D 487/14 | (2006.01) |
| C09K 19/34 | (2006.01) |
| G02B 5/30 | (2006.01) |
| G02F 1/13363 | (2006.01) |

(52) U.S. Cl.
CPC ......... *C07D 498/14* (2013.01); *Y10T 428/2848* (2015.01); *C07D 213/34* (2013.01); *C07D 239/26* (2013.01); *C07D 241/12* (2013.01); *C07D 271/107* (2013.01); *C07D 333/76* (2013.01); *C07D 487/14* (2013.01); *C09K 19/3444* (2013.01); *C09K 19/3452* (2013.01); *C09K 19/3455* (2013.01); *C09K 19/3458* (2013.01); *C09K 19/3477* (2013.01); *C09K 19/348* (2013.01); *C09K 19/3491* (2013.01); *G02B 5/3083* (2013.01); *G02F 1/133634* (2013.01); *G02F 2001/133633* (2013.01)

(58) Field of Classification Search
CPC .. C07D 213/34; C07D 239/26; C07D 241/12; C07D 271/107; C07D 333/76; C07D 487/14; C07D 498/14; C09K 19/3444; C09K 19/3452; C09K 19/3455; C09K 19/3458; C09K 19/3477; C09K 19/348; C09K 19/3491
USPC .............. 562/1; 428/354, 704, 426; 427/162; 549/43
See application file for complete search history.

(56) References Cited

U.S. PATENT DOCUMENTS

| 2,765,304 A | 10/1956 | Siegrist et al. | |
|---|---|---|---|
| 2,937,089 A * | 5/1960 | Van Allan et al. | 430/550 |
| 3,150,146 A | 9/1964 | Fields | |
| 6,482,988 B2 | 11/2002 | Fukushima et al. | |
| 2001/0044552 A1 | 11/2001 | Fukushima et al. | |
| 2004/0028839 A1* | 2/2004 | Paukshto et al. | 428/1.1 |
| 2005/0068476 A1* | 3/2005 | Okabe | 349/96 |
| 2005/0253983 A1* | 11/2005 | Carson et al. | 349/97 |

FOREIGN PATENT DOCUMENTS

| DE | 2938132 A | 9/1981 | | |
|---|---|---|---|---|
| GB | 1433130 A | 4/1976 | | |
| GB | 1441571 A | 7/1976 | | |
| GB | 2227742 A | 8/1990 | | |
| JP | 04139147 | 5/1992 | | |
| JP | 2005281259 | 10/2005 | | |
| WO | 2006025474 A | 3/2006 | | |
| WO | 2007141025 A | 12/2007 | | |
| WO | WO2007/141025 | * 12/2007 | ......... | G02F 1/13363 |
| WO | 2008020213 A | 2/2008 | | |

OTHER PUBLICATIONS

Bahadur, "Liquid Crystals—Applications and Uses," vol. 1, p. 101, World Scientific, Singapore—New York, 1990.
Lydon, "Chromonics," in Handbook of Liquid Crystals, Wiley VCH, Weinheim, 1998, vol. 28, pp. 981-1007.
Vanallan, "The Formation of Substituted Dibenzothiophene Dioxides by Sulfonation of meta- and para-Terphenyls," J. of Organic Chemistry, 1956, pp. 1152-1155.
Biermann et al. "Comparison of solvent and probe reorientation in polyacrylamide gels," XP002477471; Database CA (online), Chemical abstracts service, Columbus, Ohio, U.S. 1996, 2 pages.
Ten'Kovtsev et al., "Liquid crystalline polyesters based on 2,2'-bifluorenone-6,6'-dicarboxylic acid," XP002477472; Database CA (online), Chemical abstracts service, Columbus, Ohio, U.S. 1997, 2 pages.
Lin et al., "High H2 adsorption by coordination-framework materials," Angewandte Chemie, International edition, 2006, 45(44), pp. 7358-7364.
Morikawa et al., "Synthesis and characterization of novel aromatic polyimides from aromatic diamine and 3,3'''',4,4''''-p-quinquephenyltetracarboxylic dianhydride" Polymer Journal (Tokyo, Japan), 2002, 34(7), pp. 544-549.

(Continued)

*Primary Examiner* — Paul A Zucker
*Assistant Examiner* — Mark Luderer
(74) *Attorney, Agent, or Firm* — FisherBroyles, LLP; Adam K. Whiting (57) ABSTRACT

The polycyclic organic compounds which are substantially transparent for an electromagnetic radiation in the visible spectral range, an anisotropic optical film comprising at least one polycyclic organic compound and a method of producing thereof are disclosed. The polycyclic organic compounds have a general formula (I) wherein A and B are acid groups, n is the number of phenyl rings in the range from 3 to 10; m is 0, 1, 2 or 3; l is 1, 2, or 3, p is 1, 2, 3, 4, 5 or 6, C is a counterion from a list comprising $H^+$, $NH^+_4$, $Na^+$, $K^+$, $Li^+$, $Cs^+$, $Ca^{2+}$, $Mg^{2+}$, $Sr^{2+}$, $La^{3+}$, $Zn^{2+}$, $Zr^{4+}$, $Ce^{3+}$, $Y^{3+}$, $Yb^{3+}$, $Gd^{3+}$, and any combination thereof; k is the number of counterions necessary for compensation of the negative electric charge equal to (−p).

25 Claims, 1 Drawing Sheet

(56) References Cited

OTHER PUBLICATIONS

Morikawa "Synthesis and characterization of novel aromatic polyimides from aromatic diamine and 3,3''',4,4'''-p-quarterphenyltetracarboxylic dianhydride" Polymer Journal (Tokyo, Japan), 1999 32(3), pp. 275-279.

PCT, International Search Report and Written Opinion in International Application No. PCT/EP2008/050309, May 23, 2008, 16 pages.

* cited by examiner

Figure 1

POLYCYCLIC ORGANIC COMPOUND, OPTICALLY ANISOTROPIC FILM AND METHOD OF PRODUCTION THEREOF

This invention relates to polycyclic organic compounds which are substantially transparent for an electromagnetic radiation in the visible spectral range. Anisotropic optical films based on such compounds may be used as compensators for liquid crystal displays, and more particular, for retarders.

In recent years, Liquid Crystal Display (LCD) technology is successfully replacing Cathode Ray Tube (CRT) for applications in monitors for TVs, computers (such as, for example, notebook computers or desktop computers), watches, mobile phones etc. However, there are still some technical problems to be solved for LCDs, such as the effect of viewing angle on the coloration, contrast degradation, and brightness inversion.

Thus, technological progress poses the task of developing optical elements based on new materials with desired controllable properties. The optically anisotropic thin film is one of the solutions.

Optically anisotropic thin films are well-known in the prior art. Polyvinyl alcohol (PVA) films acquire optical anisotropy through uniaxial extension and colouring with organic dyes or iodine. However PVA-based thin films are characterised with low thermal stability which is a serious limitation for some practical applications. PVA based films are described, for example, in Liquid Crystals—Applications and Uses, B. Bahadur (ed.), World Scientific, Singapore-New York (1990), Vol. 1, p. 101.

Not only polymers, but individual chemical compounds are also capable of forming thin films in certain conditions. Some types of organic dyes are used for making thin optically anisotropic films. Films based on such dyes are formed by applying an aqueous liquid crystal (LC) solution of supramolecules formed by dye molecules onto a substrate surface with the subsequent evaporation of water. The applied films are rendered anisotropic either by preliminary mechanical orientation of the substrate surface or by applying external mechanical, electromagnetic, or other orienting forces to the LC film material on the substrate.

The ability of organic dyes to form liquid crystal phases, the methods of making the film from the dye solutions and the optical properties of dye-based thin films are described in J. Lydon, Chromonics, in Handbook of Liquid Crystals, Wiley VCH, Weinheim (1998), Vol. 2B, p. 981-1007.

Organic conjugated compounds with a molecular structure similar to the organic dye molecules but without absorption in the visible spectral range can be used for producing retarders and compensators for liquid crystal displays.
Substituted terphenyls are known in the prior art. The sulfonation of p-terphenyl with chlorosulfonic acid or 20 percent oleum at elevated temperature leads to 4'7-disulfo-3-phenyldibenzothiophene dioxide, as it was described in Journal of Organic Chemistry, 1956, pp. 1152-1155. However an anisotropic optical film cannot be formed from this derivative of p-terphenyl.

Retarders and compensators are films with phase-retarding properties in spectral regions where absorption is absent. Phase-retarding or compensating properties of such films are determined by their double refraction properties known as birefringence (Δn):

$$\Delta n = |n_o - n_e|,$$

wherein Δn is a difference of refractive indices for the extraordinary wave ($n_e$) and the ordinary wave ($n_o$). The $n_e$ and $n_o$ values vary depending on the orientation of molecules in a medium and the direction of light propagation. For example, if the direction of light propagation coincides with the optical or crystallographic axis, ordinary polarization is predominantly observed. If the light propagates in the perpendicular direction or at some angle to the optical axis, the light emerging from the medium will separate into extraordinary and ordinary components.

It is also important that, in addition to the unique optical properties, the films based on organic aromatic compounds are characterized by high environmental stability, in particular thermal stability and radiation stability (photostability).

Generally, organic conjugated compounds are poorly water soluble. But the introduction of some functional groups to the molecule can improve its water solubility—for example, some acid groups, such as various polar groups can be used for this purpose.

Compounds containing substituted oligophenyl (biphenyl and terphenyl) chains are known from the prior art. For example, in GB patent No. 1441571 para-substituted biphenyls capable of forming liquid crystal phases are described, said para-substituents are, for instance, nitro or hydroxy groups.

The introduction of two different para-substituents (i.e. alkyl and cyano) into the terminal phenyl rings of the oligophenyl chain and the ability of such compounds to form liquid crystal phases are described, for example, in GB patent No. 1433130.

In GB patent No. 2227742 compounds capable of forming liquid crystal phases in broad temperature ranges, comprising fluorinated terphenyl chains, in which para-substituents in terminal phenyl rings are alkyls, are described.

Compounds with sulfoalkyl-substituted terphenyl chains capable of forming liquid crystal layers and self-assembled monolayers on the base of such compounds are described in US Application No. 2001,044,552.

Since such optical films find use for coatings in a variety of technological applications described above, very often the environment in which they are used is characterised with high humidity and other aggressive conditions. So, there is a need for new materials for the optical thin films which are substantially transparent in visible spectral range and at the same time stable in high humidity conditions. It is also important to have a simple and reproducible manufacturing method for such optical films.

Definitions of various terms used in the description of the present invention and claims are listed below.

As used herein, the term "polycyclic organic compound" refers to a sequence of at least two substituted or unsubstituted phenyl rings which are bound as shown below in formula (I); said sequence optionally contains at least one bivalent group binding two adjacent phenyl rings by additional covalent bonds, and said sequence optionally contain at least one heterocyclic group between two adjacent phenyl rings.

The term "bivalent group" means a bridging group which can form two independent covalent bonds or, in other words, any group having two valencies available for bonding with another chemical fragment.

The term "heterocyclic group" is used for a system of one, two or three aromatic rings containing at least one heteroatom chosen from nitrogen, sulphur or oxygen, which are carbon or nitrogen linked unless specified otherwise.

The term "acid group" is used for a group capable of neutralization by aqueous alkali to form water-ionisable salt groups.

The term "thin films" defines films of thickness less than approximately 1000 microns.

In a first aspect, the present invention provides an organic compound of the general structural formula (I)

(I)

where n is the number of phenyl rings in the range from 3 to 10; A and B are acid groups; m is 0, 1, 2 or 3; l is 1, 2, or 3; p is 1, 2, 3, 4, 5 or 6; C is a counterion from a list comprising $H^+$, $NH_4^+$, $Na^+$, $K^+$, $Li^+$, $Cs^+$, $Ca^{2+}$, $Mg^{2+}$, $Sr^{2+}$, $La^{3+}$, $Zn^{2+}$, $Zr^{4+}$, $Ce^{3+}$, $Y^{3+}$, $Yb^{3+}$, $Gd^{3+}$, and any combination thereof; k is the number of counterions necessary for compensation of the negative electric charge equal to (−p). Said organic compound is transparent for an electromagnetic radiation in the visible spectral range, and a solution of said organic compound is capable of forming a substantially transparent and optically anisotropic solid layer on a substrate.

In one embodiment, said organic compound may further comprise the same or different bivalent groups $X_i$ binding two adjacent phenyl rings by additional covalent bonds, wherein i is a number in the range from 1 to (n−1) as shown in the structural formulas (III) and (IV). In another embodiment, the bivalent group is selected from the list comprising the groups —$SO_2$—, —O—, and —NH—. The acid groups A and B are independently selected from the list preferably comprising sulfonic, carboxylic and phosphonic groups.

In another embodiment of present invention, the organic compound has the structural formula (II)

(II)

In another embodiment of the present invention, the disclosed organic compound has the structural formula (III) comprising bivalent groups $X_1$, $X_2$ and $X_3$, where all the groups $X_i$ (in the formula III presented as an example i is limited to 3) are on any one side in relation to the bonds forming the chain of phenyl rings.

(III)

In another embodiment of the present invention, the disclosed organic compound has a structural formula similar to formula (III) and comprises bivalent groups $X_i$, where i can be of any value from 1 to (n−1) and all the groups $X_i$ are on any one side in relation to the bonds forming the chain of phenyl rings.

In another embodiment of the present invention, the disclosed organic compound has the structural formula (IV) comprising bivalent groups $X_1$, $X_2$ and $X_3$, where the groups $X_i$ (in the formula IV presented as an example i is limited to 3) are placed on both sides in relation to the bonds forming the chain of phenyl rings. One of the possible positions of bivalent groups in the compounds of the present invention is shown on the structural formula (IV):

(IV)

In another embodiment of the present invention, the disclosed organic compound has a structural formula similar to formula (IV) and comprises bivalent groups $X_i$, where i can be of any value from 1 to (n−1) and the groups $X_i$ are on both sides in relation to the bonds forming the chain of phenyl rings.

In the other embodiments, the polycyclic compounds of formula (I) comprise any combination of positions of the groups $X_i$ in relation to the chain of the oligophenyl ring.

In one embodiment of the present invention, the organic compound further comprises at least one heterocyclic group located between two adjacent phenyl rings. In another embodiment of the present invention, the organic compound further comprises at least two of the same or different heterocyclic groups located between two adjacent phenyl rings.

In a preferred embodiment of the organic compound, said heterocyclic groups are selected from benzodioxazole, benzodiimidazole, pyridine, pyrazine, pyrimidine, and 1,3,4-oxadiazole.

Examples of organic compounds containing at least one heterocyclic group and having general structural formulas corresponding to structures 1-6 are given in Table 1.

TABLE 1

Examples of organic compounds containing heterocyclic groups

(1)

(2)

TABLE 1-continued

Examples of organic compounds containing heterocyclic groups

The oligophenyl chain of the disclosed organic compounds provides electron conjugation sufficient for the absence of light absorption in the visible spectral range, and on the other hand, said chain provides a rigid base. The acid groups in the terminal phenyl rings give an additional possibility for orientation of the molecules which is effective for forming a liquid crystal phase.

In a second aspect, the present invention provides an anisotropic optical film on a substrate having front and rear surfaces, which comprises at least one organic layer applied onto the front surface of the substrate, wherein said layer comprises at least one organic compound of a general structural formula (I)

$$\left[ A_m \underset{}{-}\!\!\left[\underset{}{\bigcirc}\right]_{\!\!n}\!\!\underset{}{-} B_l \right]^{-p} C_k \qquad (I)$$

where n is the number of phenyl rings in the range from 3 to 10; A and B are acid groups; m is 0, 1, 2 or 3; l is 1, 2, or 3; p is 1, 2, 3, 4, 5 or 6; C is a counterion from a list comprising $H^+$, $NH^+_4$, $Na^+$, $K^+$, $Li^+$, $Cs^+$, $Ca^{2+}$, $Mg^{2+}$, $Sr^{2+}$, $La^{3+}$, $Zn^{2+}$, $Zr^{4+}$, $Ce^{3+}$, $Y^{3+}$, $Yb^{3+}$, $Gd^{3+}$, and any combination thereof; k is the number of counterions necessary for compensation of the negative electric charge equal to −p. Said organic layer is transparent for electromagnetic radiation in the visible spectral range.

In yet another embodiment of the disclosed anisotropic optical film, the organic compound may comprise the same or different bivalent groups $X_i$, binding two adjacent phenyl rings by additional covalent bonds wherein "i" is a number in the range from 1 to (n−1).

In still another embodiment of the anisotropic optical film, the organic compound comprises at least one bivalent group $X_i$ selected from the list comprising the groups —$SO_2$—, O, and —NH—.

In one embodiment of the anisotropic optical film, the acid groups A and B are independently selected from the list comprising sulfonic, carboxylic and phosphonic groups. In another embodiment of the anisotropic optical film, the organic compound has the structural formula (II), described above. In still another embodiment of the anisotropic optical film, the organic compound has the structural formula (III) comprising bivalent groups $X_1$, $X_2$ and $X_3$ described above. In another embodiment of the anisotropic optical film, the disclosed organic compound has a structural formula similar to formula (III) and comprising bivalent groups $X_i$, where i can be of any value from 1 to (n−1) and all the groups $X_i$ are on any one side in relation to the bonds forming the chain of phenyl rings.

In yet another embodiment of the anisotropic optical film, the organic compound has the structural formula (IV) comprising bivalent groups $X_1$, $X_2$ and $X_3$ described above. In another embodiment of the anisotropic optical film, the disclosed organic compound has a structural formula similar to formula (IV) and comprising bivalent groups $X_i$, where i can be of any value from 1 to (n−1) and the groups $X_i$ are on both sides in relation to the bonds forming the chain of phenyl rings.

In the other embodiments, the polycyclic compounds of formula (I) comprise any combination of positions of the groups $X_i$ in relation to the chain of the oligophenyl ring.

In one embodiment of the present invention, the anisotropic optical film comprises a compound of formula (I) in which at least one heterocyclic group is located between two adjacent phenyl rings. In another embodiment of the anisotropic optical film, the organic compound further comprises at least two of the same or different heterocyclic groups located between two adjacent phenyl rings. In a preferred embodiment of the anisotropic optical film, said heterocyclic groups are selected from benzodioxazole, benzodiimidazole, pyridine, pyrazine, pyrimidine, and 1,3,4-oxadiazole.

In one embodiment of anisotropic optical film, the organic compound is selected from compounds having a general structural formula corresponding to structures 1-6 are given in Table 1.

TABLE 1

Examples of organic compounds containing heterocyclic groups

In another embodiment, the anisotropic optical film is substantially insoluble in water and/or in water-miscible solvents.

In still another embodiment of the anisotropic optical film according to this invention, said organic layer is a biaxial retardation layer possessing one refraction index (nz) in the normal direction to the substrate surface and two refraction indices (nx and ny) corresponding to two mutually perpendicular directions in the plane of the substrate surface. In yet another embodiment, the refractive indices nx, ny and nz obey the following condition: nx<nz<ny In still another embodiment of the disclosed anisotropic optical film, the substrate is transparent for electromagnetic radiation in the visible spectral range. In still another embodiment, the substrate is made of a polymer. In yet another embodiment of the disclosed anisotropic optical film, the substrate is made of a glass.

The disclosed invention also provides an anisotropic optical film further comprising an additional adhesive transparent layer placed on top of said anisotropic optical film. In another embodiment of the invention the anisotropic optical film further comprises an additional transparent adhesive layer placed on top of the anisotropic optical film. In one embodiment of the disclosed invention, the anisotropic optical film further comprises a protective coating formed on the adhesive transparent layer.

In still another embodiment of the disclosed invention, the anisotropic optical film comprises two or more organic layers, wherein each of these layers comprises different polycyclic organic compounds of the general structural formula (I),
ensuring the absorption of electromagnetic radiation in at least one predetermined wavelength subrange of the UV spectral range.

The present invention also provides a film which is characterised with a high stability in humid environments.

In a third aspect, the present invention provides a method of producing an anisotropic optical film on a substrate, which comprises the following steps:

(1) preparation of a solution of a polycyclic organic compound of the general structural formula (I) or a combination of such compounds where n is the number of phenyl rings in the range from 3 to 10; A and B are acid groups; m is 0, 1, 2 or 3; l is 1, 2, or 3; p is 1, 2, 3, 4, 5 or 6; C is a counterion selected from the list comprising $H^+$, $NH^+_4$, $Na^+$, $K^+$, $Li^+$, $Cs^+$, $Ca^{2+}$, $Mg^{2+}$, $Sr^{2+}$, $La^{3+}$, $Zn^{2+}$, $Zr^{4+}$, $Ce^{3+}$, $Y^{3+}$, $Yb^{3+}$, $Gd^{3+}$, and any combination thereof; k is the number of counterions necessary for compensation of the negative electric charge equal to −p; wherein said organic compound is transparent for electromagnetic radiation in the visible spectral range;

(2) application of a liquid layer of the solution on the substrate; and (3) drying with the formation of a solid layer.

In one embodiment of the disclosed invention, said method further comprises the step of applying an external alignment action upon the liquid layer of the solution simultaneously with the application of a liquid layer or after the application step but prior to the drying step. The external alignment action may be produced by mechanical forces such as a shearing force applied when the solution is spread on the surface by any tool, selected from the list comprising a Mayer rod (a cylindrical rod wound with a wire), a slot-die or any other technique known in the art. Besides mechanical forces, one may use an application of electrical, electro-magnetical, gravitational forces or any others which allow orienting of the film on the substrate in the mode required.

In one embodiment the present invention provides a relatively simple and inexpensive method for fabricating organic anisotropic optical films with phase-retarding properties, in particular optical retarders or compensators. In another embodiment the present invention provides the method of an application of a liquid layer onto a substrate via printing of an aqueous solution. In still another embodiment of present invention, a low concentration of a liquid crystal solution used for LLC phase formation provides for the possibility of the manufacture of thin optical films. In one embodiment the present invention provides a method of formation of water-insoluble thin optical films. In another embodiment the present invention provides a film characterised with a low sensitivity to humidity variations, which ensures high environmental stability of the obtained films.

In another embodiment of the disclosed method, said solution also ensures the absorption maxima of electromagnetic radiation in at least one predetermined wavelength subrange of the UV spectral range. A part of the UV spectral range in which the solution absorbs electromagnetic radiation will be called a subrange.

In yet another embodiment of the disclosed method, the organic compound may comprise the same or different bivalent groups $X_i$, binding two adjacent phenyl rings by additional covalent bonds wherein "i" is a number in the range from 1 to (n−1).

In one embodiment of the disclosed method, the acid groups A and B in the compound of the general structural formula (I) are independently selected from the list comprising the sulfonic, carboxylic and phosphonic groups. In another embodiment of the disclosed method, the organic compound has the structural formula (II) described above.

In still another embodiment of the method of the present invention, the organic compound has the structural formula (III) comprising bivalent groups $X_1$, $X_2$ and $X_3$ described above. In another embodiment of the method of the present invention, the disclosed organic compound has a structural formula similar to formula (III) and comprises bivalent groups $X_i$, where i can be of any value from 1 to (n−1) and all the groups $X_i$ are on any one side in relation to the bonds forming the chain of phenyl rings.

In yet another embodiment of the method of the present invention, the organic compound has the structural formula (IV) comprising bivalent groups $X_1$, $X_2$ and $X_3$ described above. In another embodiment of the method of the present invention, the disclosed organic compound has a structural formula similar to formula (IV) and comprises bivalent groups $X_i$, where i can be of any value from 1 to (n−1) and the groups $X_i$ are on both sides in relation to the bonds forming the chain of phenyl rings.

In other embodiments of the method of the present invention, the polycyclic compounds of formula (I) comprise any combination of positions of the groups $X_i$ in relation to the chain of oligophenyl ring.

In one embodiment of the present invention, the disclosed method further comprises at least one heterocyclic group located between two adjacent phenyl rings of the organic compound. In another embodiment of the method of the present invention, the organic compound further comprises at least two of the same or different heterocyclic groups located between two adjacent phenyl rings. In one preferred embodiment, said heterocyclic groups are selected from benzodioxazole, benzodiimidazole, pyridine, pyrazine, pyrimidine, and 1,3,4-oxadiazole.

In one embodiment of the disclosed method, the organic compound is selected from the compounds having a general structural formula corresponding to structures 1-6 are given in Table 1.

TABLE 1

Examples of organic compounds containing heterocyclic groups

TABLE 1-continued

Examples of organic compounds containing heterocyclic groups

In the embodiments wherein at least one acid group is $SO_3^-$, the method preferably comprises an additional step of treating the film with a metal salt solution comprising a cation selected from the list comprising $Ba^{(2+)}$, $Pb^{2+}$ and $Sr^{2+}$ cations.

In yet another embodiment of the disclosed method, the solution is an aqueous solution based on water and/or water-miscible solvents.

In another embodiment of the present invention, the substrate is pre-treated so as to render its surface hydrophilic.

In still another embodiment of the disclosed method, said aqueous solution is a lyotropic liquid crystal solution.

In other embodiment, the drying step is carried out under an elevated temperature. In a preferred embodiment, the temperature is in the range from approximately 20 to 60 centigrade.

In still another embodiment, the sequence of technological operations of the application of the liquid layer of the solution, the alignment step and the drying step are repeated two or more times and each consequent solid layer is formed using the aqueous solution being either the same or different from that used in the previous cycle.

Other objects and advantages of the present invention will become apparent upon reading the following detailed description of the examples and the appended claims provided below, and upon reference to the drawing, in which:

The following examples are detailed descriptions of methods of preparation and use of certain compounds of the present invention. The examples are presented to illustrate the embodiments of the invention and are not intended as a restriction on the scope of the invention. In the following examples, all percentages are weight percentages and all temperatures are in centigrade.

EXAMPLE 1

Example 1 describes the preparation of the polycyclic organic compound of formula (ii)

(II)

A 4,4'-(5,5-Dioxidodibenzo[b,d]thiene-3,7-diyl)dibenzenesulfonic acid (II) was prepared by sulfonation of 1,1':4',1":4",1'''-quaterphenyl. 1,1':4',1":4",1'''-quaterphenyl (10 g) was charged into 0%-20% oleum (100 ml). Reaction mass was agitated for 5 hours at heating or at ambient conditions. After that the reaction mixture was diluted with water (170 ml). The final sulfuric acid concentration became approximately 55%. The precipitate was filtered and rinsed with glacial acetic acid (~200 ml). The filter cake was dried in an oven at about 110° C. The process yielded 8 g of 4,4'-(5,5-Dioxidodibenzo[b,d]thiene-3,7-diyl)dibenzenesulfonic acid.

The product was analyzed with $^1H$ NMR (Brucker Avance-600, DMSO-$d_6$, δ, ppm) and showed the following results: 7.735 (d, 4H, $4CH^{Ar}(3,3',5,5')$); 7.845 (d, 4H, $4CH^{Ar}(2,2',6,6')$); 8.165 (dd, 2H, $2CH^{Ar}(2,8)$); 8.34 (m, 4H, $4CH^{Ar}(1,9,4,6)$). The electronic absorption spectrum of the product measured in an aqueous solution with spectrometer UV/VIS Varian Cary 500 Scan showed the absorption maxima at $\lambda_{max1}=218$ nm ($\epsilon=3.42*10^4$), $\lambda_{max2}=259$ nm ($\epsilon=3.89*10^4$), and $\lambda_{max3}=314$ nm ($\epsilon=4.20*10^4$). The mass spectrum of the product recorded using a Brucker Daltonics Ultraflex TOF/TOF is as follows: molecular ion ($M^-=529$), FW=528.57.

EXAMPLE 2

Example 2 describes the preparation of an anisotropic optical film formed from a lyotropic liquid crystal solution.

A 4,4'-(5,5-Dioxidodibenzo[b,d]thiene-3,7-diyl)dibenzenesulfonic acid (1 g) was obtained as described in Example 1, then was mixed with 3.8 ml of distilled water and 1.1 ml of 10% aqueous sodium solution and then stirred at room temperature (23° C.) until a lyotropic liquid solution was formed (for approximately 1 hour).

An LCD-grade Soda Lime glass substrate was prepared for the coating. The substrate was placed in an ultrasonic bath with an aqueous solution of NaOH (w/w 10%) and $KMnO_4$ (w/w 0.1%) for 30 min, then rinsed with deionised water, and dried with a compressed air stream. The lyotropic liquid crystal solution was applied onto the pretreated glass substrate with Mayer Rod #1.5 moved at linear velocity of 200 mm/s (humidity=30%, temperature=23° C.). The coated solution was further dried with the compressed air stream until the anisotropic optical film was formed.

Figure 1:
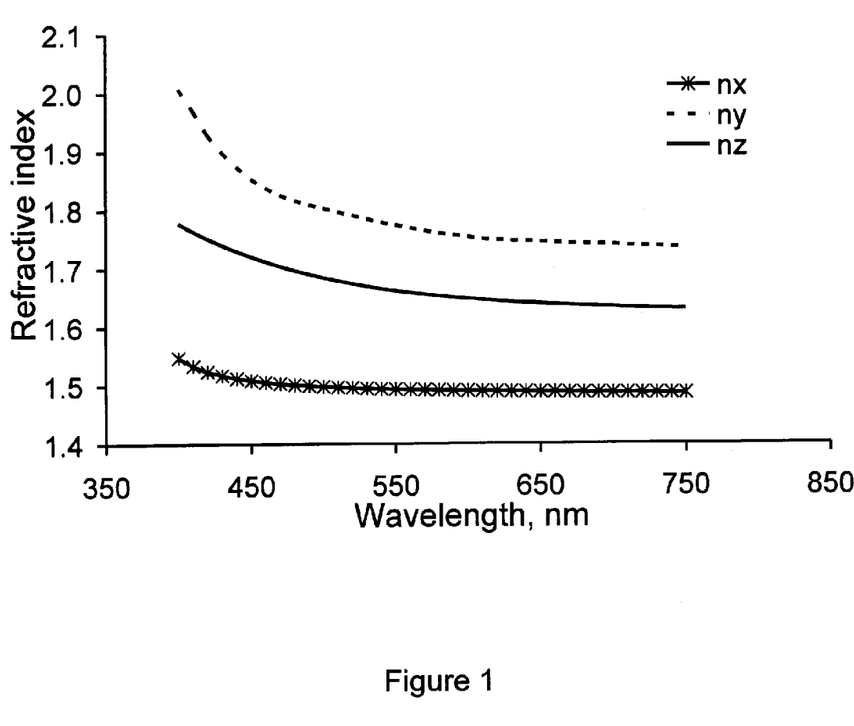
FIG. 1 shows a wavelength dependence of refractive indices for a thin birefringent plate based on a compound of formula (II).

The thickness of the produced anisotropic optical film was in the range from 420 to 450 μm. Said thickness may be regulated by varying the concentration of the organic compound in the water solution. The anisotropic optical film formed is clear (colourless) and transparent in the optical spectral range. FIG. 1 shows wavelength dependence of refractive indices for the anisotropic optical film formed according to present invention.

The invention claimed is:

1. A polycyclic organic compound of structural formula (Ib)

wherein
A and B are acid groups independently selected from the list consisting of sulfonic and carboxylic; m is 0 or 1; and l is 1;
C is a counterion selected from the list consisting of $H^+$, $NH^+_4$, $Na^+$, $K^+$, $Li^+$, $Cs^+$, $Ca^{2+}$, $Mg^{2+}$, $Sr^{2+}$, $La^{3+}$, $Zn^{2+}$, $Zr^{4+}$, $Ce^{3+}$, $Y^{3+}$, $Yb^{3+}$, $Gd^{3+}$, and any combination thereof; k is the number of counterions necessary for compensation of the negative electric charge equal to (−p); and p is 1, 2, 3, 4, 5 or 6;
X is a bivalent group selected independently from the group consisting of —$SO_2$—, —O—, and —NH—;
wherein said organic compound is transparent for electromagnetic radiation in the visible spectral range.

2. An organic compound according to claim 1, wherein the compound has the structural formula (II):

3. A polycyclic organic compound of structural formula (III)

wherein
A and B are acid groups independently selected from the list consisting of sulfonic and carboxylic; m is 0 or 1; and l is 1;
C is a counterion selected from the list consisting of $H^+$, $NH^+_4$, $Na^+$, $K^+$, $Li^+$, $Cs^+$, $Ca^{2+}$, $Mg^{2+}$, $Sr^{2+}$, $La^{3+}$, $Zn^{2+}$, $Zr^{4+}$, $Ce^{3+}$, $Y^{3+}$, $Yb^{3+}$, $Gd^{3+}$, and any combination thereof; k is the number of counterions necessary for compensation of the negative electric charge equal to (−p); and p is 1, 2, 3, 4, 5 or 6;
$X_1$, $X_2$, and $X_3$, each is a bivalent group selected independently from the group consisting of —$SO_2$—, —O—, and —NH—;
wherein said organic compound is transparent for electromagnetic radiation in the visible spectral range.

4. A polycyclic organic compound of structural formula (IV)

wherein
A and B are acid groups independently selected from the list consisting of sulfonic and carboxylic; m is 0 or 1; and l is 1;
C is a counterion selected from the list consisting of $H^+$, $NH^+_4$, $Na^+$, $K^+$, $Li^+$, $Cs^+$, $Ca^{2+}$, $Mg^{2+}$, $Sr^{2+}$, $La^{3+}$, $Zn^{2+}$, $Zr^{4+}$, $Ce^{3+}$, $Y^{3+}$, $Yb^{3+}$, $Gd^{3+}$, and any combination thereof; k is the number of counterions necessary for compensation of the negative electric charge equal to (−p); and p is 1, 2, 3, 4, 5 or 6; and
$X_1$, $X_2$, and $X_3$, each is a bivalent group selected independently from the group consisting of —$SO_2$—, —O—, and —NH—;
wherein said organic compound is transparent for electromagnetic radiation in the visible spectral range.

5. An anisotropic optical film, which comprises at least one organic layer comprising at least one polycyclic organic compound of a structural formula (I)

wherein
n is the number of phenyl rings from 4 to 6;
A and B are acid groups independently selected from the list consisting of sulfonic and carboxylic; m is 0 or 1; and l is 1;
C is a counterion selected from the list consisting of $H^+$, $NH^+_4$, $Na^+$, $K^+$, $Li^+$, $Cs^+$, $Ba^{2+}$, $Ca^{2+}$, $Mg^{2+}$, $Sr^{2+}$, $La^{3+}$, $Zn^{2+}$, $Zr^{4+}$, $Ce^{3+}$, $Y^{3+}$, $Yb^{3+}$, $Gd^{3+}$, and any combination thereof; k is the number of counterions necessary for compensation of the negative electric charge equal to (−p); and p is 1, 2, 3, 4, 5 or 6;
wherein the organic compound comprises a bivalent group $X_i$, that covalently binds to two adjacent phenyl rings as in structural formula (Ia)

wherein X is selected independently from the group consisting of —$SO_2$—, —O—, and —NH—, and i is the number of bivalent groups from 1 to (n−1);

and wherein said organic layer is transparent for electromagnetic radiation in the visible spectral range.

6. An anisotropic optical film according to claim 5, wherein said organic compound has the structural formula (II)

(II)

7. An anisotropic optical film according to claim 5, wherein said organic compound comprises structural formula (III)

(III)

8. An anisotropic optical film according to claim 5, wherein said organic compound comprises structural formula (IV):

(IV)

9. An anisotropic optical film according to claim 5, wherein said anisotropic film is insoluble in water and/or in water-miscible solvents.

10. An anisotropic optical film according to claim 5, wherein said organic layer is a biaxial retardation layer possessing one refractive index (nz) in the normal direction to the layer and two refractive indices (nx and ny) corresponding to two mutually perpendicular directions in the plane of the layer.

11. An anisotropic optical film according to claim 10, wherein the refractive indices nx, ny and nz obey the following condition: ny>nz>nx.

12. An anisotropic optical film according to claim 5, wherein the organic layer is on a substrate made of a polymer or glass which is transparent for electromagnetic radiation in the visible spectral range.

13. An anisotropic optical film according to claim 5, further comprising an additional transparent adhesive layer applied on top of the organic layer.

14. An anisotropic optical film according to claim 13, further comprising a protective coating applied on the adhesive transparent layer.

15. An anisotropic optical film according to claim 5 comprising two or more said organic layers, wherein the layers comprise different polycyclic organic compounds as defined by claim 5.

16. A method of producing an anisotropic optical film on a substrate comprising the steps of a) preparation of a solution of a polycyclic organic compound of the general structural formula (I) or any combination of such compounds of structural formula (I)

(I)

wherein n is the number of phenyl rings from 4 to 6;

A and B are acid groups independently selected from the list consisting of sulfonic and carboxylic; m is 0 or 1; and l is 1;

C is a counterion selected from the list consisting of $H^+$, $NH^+_4$, $Na^+$, $K^+$, $Li^+$, $Cs^+$, $Ba^{2+}$, $Ca^{2+}$, $Mg^{2+}$, $Sr^{2+}$, $La^{3+}$, $Zn^{2+}$, $Zr^{4+}$, $Ce^{3+}$, $Y^{3+}$, $Yb^{3+}$, $Gd^{3+}$, and any combination thereof; k is the number of counterions necessary for compensation of the negative electric charge equal to (−p); and p is 1, 2, 3, 4, 5 or 6;

wherein the organic compound comprises a bivalent group $X_i$, that covalently binds to two adjacent phenyl rings as in structural formula (Ia)

(Ia)

wherein X is selected independently from the group consisting of —$SO_2$—, —O—, and —NH—, and i is the number of bivalent groups from 1 to (n−1); and wherein said organic compound is transparent for electromagnetic radiation in the visible spectral range, b) application of a liquid layer of the solution onto the substrate, c) application of an external alignment action upon the solution simultaneous with or after step b) but prior to step d), and d) drying with the formation of a solid layer.

17. A method according to claim 16, wherein said organic compound has the structural formula (II)

(II)

18. A method according to claim 16, wherein said organic compound comprises structural formula (III)

(III)

19. A method according to claim 16, wherein said organic compound comprises structural formula (IV):

(IV)

20. A method according to claim 16, wherein said solution is an aqueous solution comprising water and/or water-miscible solvents.

21. A method according to claim 16, wherein the drying is executed in an airflow at an elevated temperature in the range from approximately 20 to 60 centigrade.

22. A method according to claim 16, wherein said organic compound comprises sulfonic groups and said formed solid layer and is treated with a metal salt solution.

23. A method according to claim 16, wherein the metal salt comprises a cation selected from the list consisting of $Ba^{2+}$, $Pb^{2+}$, and $Sr^{2+}$ cations.

24. A method according to claim 16, wherein said solution is a lyotropic liquid crystal solution.

25. A method according to claim 16, wherein the sequence of technological operations of the application of the solution, the alignment action and the drying is repeated two or more times and each consequent solid layer is formed using the aqueous solution, this solution being either the same or different from that used in the previous cycle.

* * * * *